United States Patent [19]
Ono

[11] Patent Number: 4,571,023
[45] Date of Patent: Feb. 18, 1986

[54] DEVICE FOR OBSERVING PICTURES

[75] Inventor: Kimizo Ono, Osaka, Japan

[73] Assignee: Sumitomo Electric Industries, Ltd., Japan

[21] Appl. No.: 597,487

[22] Filed: Apr. 6, 1984

[30] Foreign Application Priority Data

Apr. 11, 1983 [JP] Japan ................................. 58-63469
Apr. 11, 1983 [JP] Japan ............................. 58-53822[U]

[51] Int. Cl.⁴ .............................................. G02B 6/06
[52] U.S. Cl. ............................. 350/96.25; 350/96.15; 350/96.18
[58] Field of Search ................. 350/96.15, 96.18, 96.25

[56] References Cited

U.S. PATENT DOCUMENTS

| | | | |
|---|---|---|---|
| 1,877,109 | 9/1932 | Wullenweber | 350/618 |
| 2,507,935 | 5/1950 | Richmond | 350/618 |
| 3,643,654 | 2/1972 | Felbarg | 350/618 |
| 3,804,081 | 4/1974 | Kinoshita et al. | 350/96.25 |
| 3,856,000 | 12/1974 | Chikama | 350/96.26 |
| 4,154,502 | 5/1979 | Siegmund | 350/96.25 |
| 4,156,556 | 5/1979 | Klein et al. | 350/96.18 |
| 4,328,488 | 5/1982 | Yanai et al. | 350/96.18 |
| 4,469,941 | 9/1984 | Palmer | 350/96.15 |

Primary Examiner—William L. Sikes
Assistant Examiner—Robert E. Wise
Attorney, Agent, or Firm—Ernest A. Beutler

[57] ABSTRACT

A device for observing pictures of an object is proposed which has an image transmission line for transmitting an image, an optical system for forming the image of the object at the front end of said image transmission line, a reflex mirror for reflecting the light from the object and directing it toward said optical system, a flexible cable accommodating said image transmission line, and an image receiving means provided at an end of said image transmission line for observing the image transmitted, said image transmission line having an image fiber comprising a bundle of picture element fibers.

6 Claims, 11 Drawing Figures

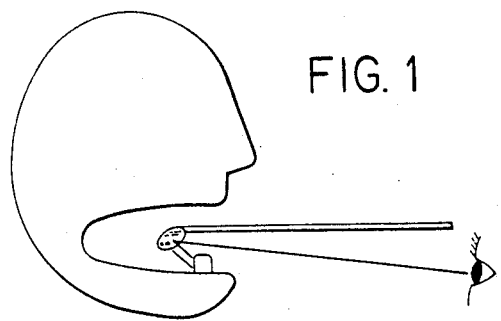
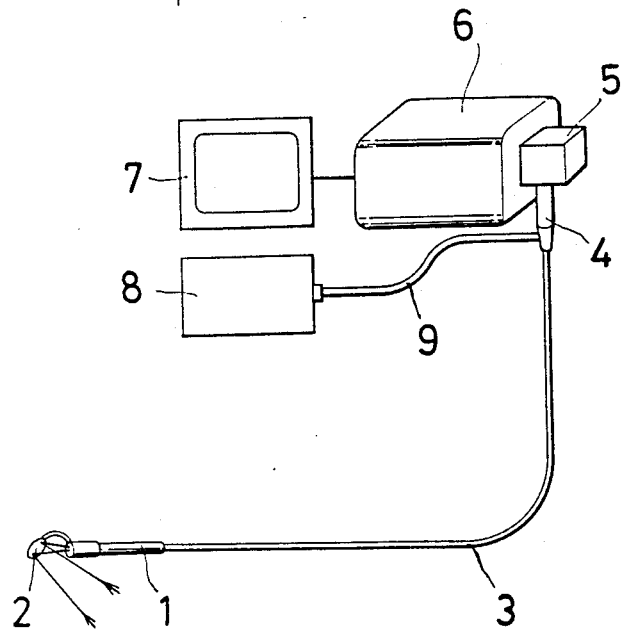
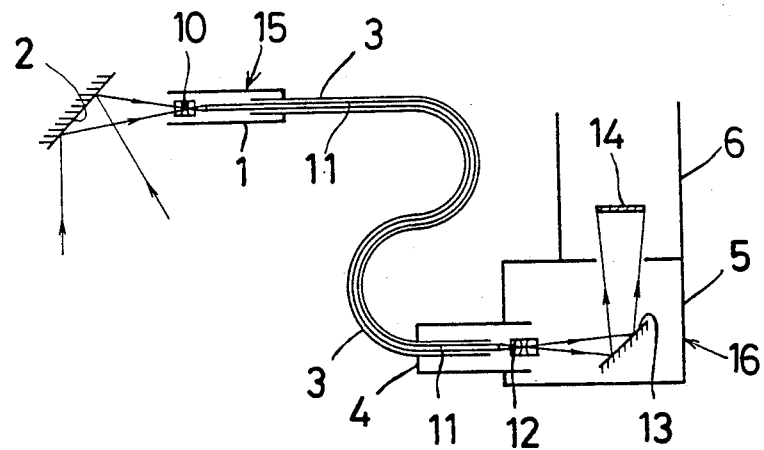

DEVICE FOR OBSERVING PICTURES

The present invention relates to a device for observing pictures used for the observation of confined portions such as an oral cavity in dental or other medical treatments. This device is also applicable for industrial use such as for the maintenance of equipment, and for civil engineering and construction work.

A drawback contingent to the observation of an image reflected in a mirror is that the mirror image is reversed bilaterally from the actual image. The inspection of an oral cavity conducted by a dentist or a nose, ear and throat specialist will be taken as an example to explain this drawback.

As shown in FIG. 1, a bar with a reflex mirror mounted on its end with an angle of inclination has been used to inspect an oral cavity. It permits the inspection of a portion which cannot be seen directly in the oral cavity, such as the back side of a tooth, because the light from the back side of the tooth is reflected by the reflex mirror and comes into the eye of a dentist. This appliance is easy to handle because it is light in weight and small in size. Therefore, with this appliance an oral cavity can be inspected easily.

However, this method has the following disadvantage:

(1) An image is bilaterally reversed as mentioned above.

(2) The object is not so well lit. In other words, it is often hard to see an object because of dimness.

(3) It is difficult to see a narrow region. Because the conventional appliance has no means for magnifying an object, you have to bring the eye close to the oral cavity of a patient for detailed inspection of a narrow region. However, there is a limit in doing so.

(4) The affected part cannot be inspected by a plurality of persons at a time, but only by a single dentist. The patient cannot see the affected part with his own eyes. Therefore, he cannot receive treatment with his understanding and consent. A plurality of physicians cannot inspect the same seat of a disease at a time to discuss about the diagnosis and treatment.

Such a bilateral reversal does not embarrass a person so much when he inspects with such a simple appliance as shown in FIG. 1. However, when a dentist inspects an oral cavity by means of a large-scale observation device, it will be strange to look at a bilaterally reversed image projected on a large screen of a video monitor. It will be natural that he wishes an image not reversed on the screen.

It is an object of the present invention to provide a device for observing pictures which obviates the abovedescribed disadvantages.

The device for observing pictures in accordance with the present invention comprises an image transmission line, an optical system for forming the image of an object at the front end of the image transmission line, a reflex mirror for reflecting the light from the object to direct it toward the optical system, a flexible cable having the image transmission line therein, and an image-receiving optical system provided at the rear end of the image transmission line for the inspection of the transmitted image, wherein the image transmission line is provided by an image fiber comprising a bundle of picture element fibers. A feature of the present invention is that by reflecting an image in an even number of times, no bilateral reversal will occur.

Another feature of the present invention is that the reflex mirror used is not in a perfectly circular form but in the form of an elongated closed curve such as an oval, ellipse or the like with its minor axis at a right angle to the image transmission line.

The above-described and other objects and features of this invention will be readily appreciated as the same becomes better understood by reference to the following detailed description when considered in connection with the accompanying drawings, in which:

FIG. 1 is a view illustrating a conventional device of inspecting an oral cavity;

FIG. 2 is a schematic view of the entire device in accordance with the present invention;

FIG. 3 is a schematic view of an embodiment in which a reflex mirror is added in the image-receiving unit;

Figure 4:
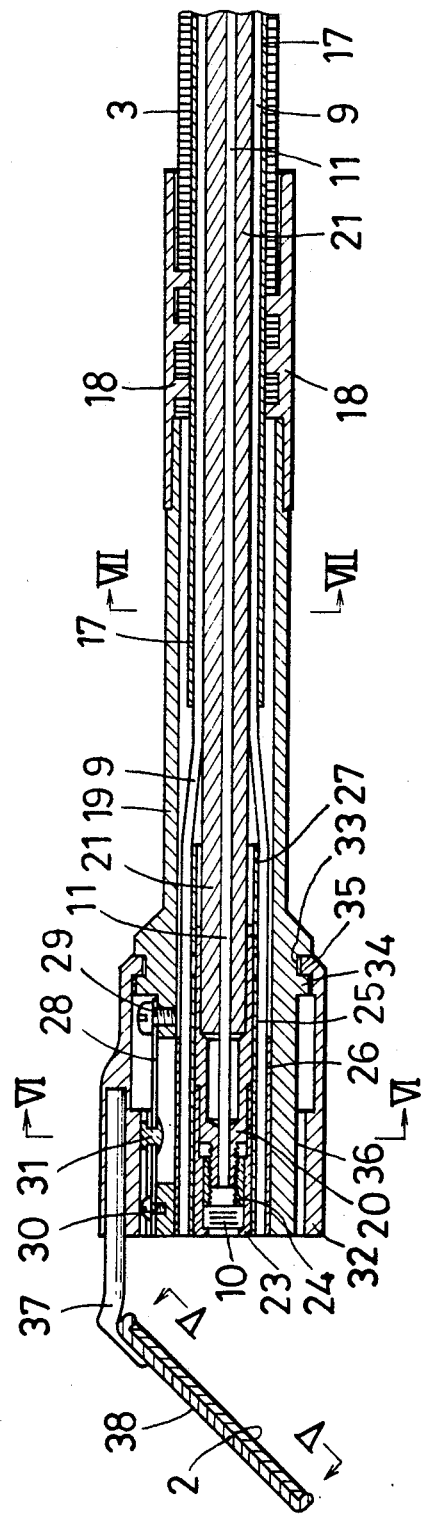
FIG. 4 is a longitudinal section of a probe used in the device in accordance with the present invention.
Figure 7:
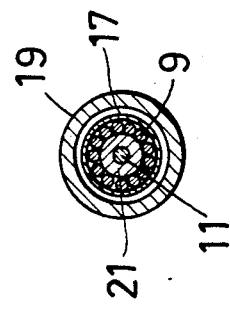
FIG. 7 is a sectional view taken along line VII—VII of FIG. 4.
Figure 6:
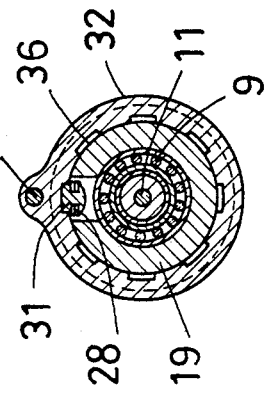
FIG. 6 is a sectional view taken along line VI—VI of FIG. 4.
Figure 5:
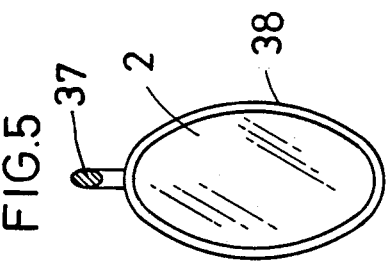
FIG. 5 is a view taken in the direction of arrows V—V of FIG. 4.

Referring now to FIG. 2, a probe 1 accommodates an image fiber for transmitting an image and a light guide for transmitting the light for illumination, and an optical system for forming the image of an object being inspected at the end of the image fiber. A reflex mirror 2 is mounted in front of the probe 1 at an angle on the extension of the optical axis of the image fiber. The light for illumination is projected from the light guide and reflected by the reflex mirror 2 to illuminate the object. The light from the object is reflected by the reflex mirror 2 and focused by a lens at the end of the image fiber. The image fiber and the light guide run parallel with each other in a flexible cable 3 and are connected to an image-receiving adapter 4.

The image transmitted by the image fiber is picked up by a TV camera 6 through an optical system 5 coupled therewith, and is projected on the screen of a TV monitor 7.

The light from a light source 8 for illumination, such as a halogen lamp, is transmitted through a light guide 9 and the light guide in the flexible cable 3 and reaches the object via the reflex mirror 2. Instead of being projected on the screen of the TV monitor 7, the image picked up by the TV camera 6 may be recorded in a video tape recorder.

A feature of the present invention is that an even number of reflex mirrors are used to reflect the light from the object in the even number of times before an image comes to a viewer.

This can be done in the following three manners:

(1) Another mirror is added between the reflex mirror 2 and the probe 1. The light from the object is reflected by the two mirrors so that the image incident on the end of the probe will not be a reversed one.

(2) An optical device for the reversal of an image, which includes an odd number of reflex mirrors and an optical system, is added in the intermediate portion of the flexible cable 3. Such an optical device may comprise, e.g., a lens and a prism or prisms serving as reflex mirrors.

(3) Another reflex mirror is added in the image-receiving unit.

In short, one or an odd number of reflex mirrors may be added in a suitable position in the light path.

FIG. 3 illustrates an embodiment in which a reflex mirror for the reversal of an image is added in the image-receiving unit. The light guide is omitted. No light guide has to be provided when some other means for supplying illumination light is available. Only an image pick-up unit 15 and an image-receiving unit 16 are illustrated. A lens assembly 10 is provided to form the image of the object at the front end of an image fiber 11.

The image transmitted through the image fiber 11 is bilaterally reversed. In the image-receiving unit 16, a lens 12 and a reflex mirror 13 are provided in the optical system 5 coupled with the TV camera 6. The image reflected by the reflex mirror 13 is incident on a surface 14 of the TV camera 6. The reflex mirror 13 is a newly added optical element. The image, which has already been bilaterally reversed, is further subjected to a bilateral reversal by the mirror 13 back to the actual shape of the object.

The reflex mirror 13 changes the direction in which the light travels. Therefore, the image-receiving adapter 4 is connected to the TV camera 6 so that the axis of the former will be at a right angle to the axis of the latter.

Refering now to FIGS. 4 to 7, the probe 1 for the inspection of images is provided on the end of the flexible cable 3 which accommodates in its center the image fiber 11 for transmitting an image and a plurality of light guides 9 disposed around the image fiber. A covering tube 17 is interposed between the flexible tube 3 and the light guides 9. The flexible tube 3 is coupled with the probe 1 by a flexible joint 18 provided at the rear end of the probe.

The body 19 of the probe 1 is a cylindrical pipe made of stainless steel, to the rear end of which the flexible joint 18 is secured. The image fiber 11 and light guides 9 extend forwardly in the body 19 of the probe. The light guides run to the front end of the probe and are open to the exterior. The covering 21 of the image fiber 11 is peeled off at its front end. Its exposed end is kept in position by a jig 20.

A lens assembly 22 is supported in front of the image fiber by a cylindrical lens mount 23 and a lens holder 24. The lens holder threadedly engages the jig 20, and the lens mount 23 threadedly engages the lens holder 24.

Jigs 25 and 26 are disposed inside and outside the light guides 9, respectively, to protect them. A protective tube 27 is interposed between the rear end of the jig 20 and the light guides 9. The body 19 of the probe is provided with a longitudinal groove in its bell-shaped front end to receive a leaf spring 28 elastically supported by screws 29 and 30. A stop pin 31 disposed at the intermediate portion of the leaf spring 28 prevents an end cover 32 from turning on its own axis.

The cylindrical end cover 32 serves to mount a mirror on the probe. An annular groove 33 is provided in the external surface of the probe body 19. Outside of the groove 33 there are several projections 34. The end cover 32 is also provided at its rear end with several projections 35. The projections 35 are passed through the spaces between the projections 34 and the cover 32 is slightly rotated. Now the projections 35 engage the projections 34 so as to prevent the end cover 32 from coming out of the probe body 19.

The end cover 32 is provided with grooves 36 in its inner surface. Prevention of the end cover 32 from rotation is effected by allowing the head of the stop pin 31 to slip into one of the grooves 36. When the end cover 32 is forcibly turned against the resilience of the leaf spring 28, the stop pin 31 slips out of the groove.

A mirror mounting rod 37 projects frontwardly from the end of the end cover 32. A mirror mount 38 is welded to the mirror mounting rod 37. A mirror 2 is secured to the mirror mount 38. The center of the mirror 2 lies on the extension of the image fiber 11. However, the axis of the image fiber has not necessarily to be exactly aligned with the center of the mirror. The surface of the mirror forms an angle of $\theta$ with the axis of the image fiber. Although $\theta$ is equal to 45° in this embodiment, it may not be 45°.

What is important is that the mirror 2 is elliptical. The minor axis of this elliptical mirror is perpendicular to the axis of the image fiber, while its major axis forms an angle of $\theta$ with the axis of the image fiber.

In an embodiment of the mirror 2, the major axis is 25 mm long and the minor axis is 15 mm. It is narrower in width by 10 mm than a perfectly circular mirror having a diameter of 25 mm. But, this does not affect the quantity of light coming into the image fiber 11 and the broadness of the visual field.

Figure 8:
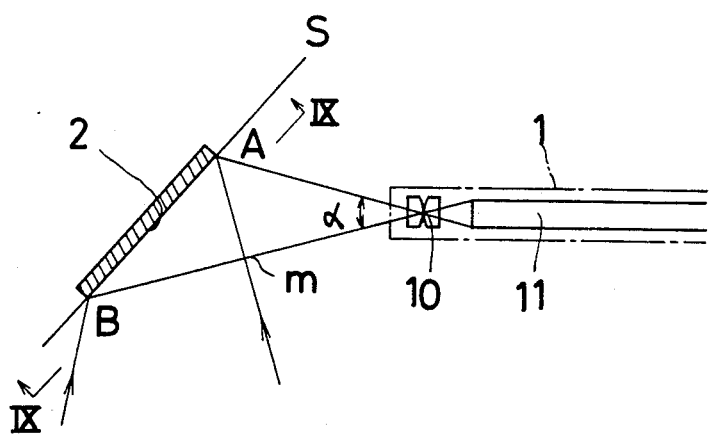
FIG. 8 is a schematic view of the end of the probe and the mirror.

Referring to FIG. 8, the probe 1 accommodates an image fiber 11 and lenses 10. The image fiber has a circular section. Therefore, only a conic portion of the light reflected by the mirror 2 is focussed by the lens assembly 10 into the end of the image fiber. In other words, only the light falling within a cone m having a vertical angle of $\alpha$ and its vertex disposed in the center of the lens assembly 10 comes into the image fiber.

Figure 9:
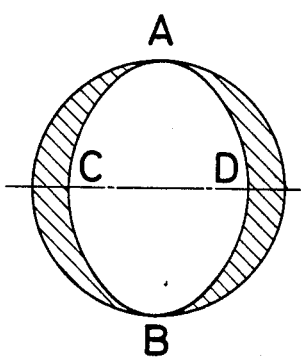
FIG. 9 is a view showing how the surface of the mirror is divided into utilizable (blank) and unutilizable (hatched) areas.

The light reflected in the range between A and B in the vertical section of the mirror is utilized. In the direction perpendicular to AB, however, the light reflected in a narrower range falls within the cone m. FIG. 9 illustrates the mirror surface. The blank area falls within the cone m, while the hatched area does not fall. The area falling within the cone is in the form of an elongated circle having a major axis AB and a minor axis CD.

The hatched area is an area which cannot be utilized as a mirror because the light reflected by this area is not focused within the end face of the image fiber. Therefore, the mirror may be in the form of an elongated circle ADBC. A mirror without the useless hatched area is narrower and thus is easily inserted into a confined portion.

The ideal shape of the mirror will be discussed below. In FIG. 8, the cone m of light has its vertex disposed in the lens assembly and has a vertical angle of $\alpha$. Now the shape of a curved line at which the cone m intersects the mirror surface S will be discussed below.

A cone can be expressed in a quadratic formula with coordinates x, y and z in a rectangular coordinate system. A plane can be expressed in a linear formula with coordinates x, y and z. Therefore, an equation representing the curved line at which the cone m intersects the plane S is obtained by solving simultaneous equations consisting of the above-mentioned quadratic and linear formulas. By eliminating any one of three variables from the simultaneous equations, a quadratic formula having the remaining two variables is obtained.

A quadratic equation represents an ellipse, a hyperbola or a parabola. In the present case, it is essential that the edge of a mirror be in the form of a closed curve, from which it will be understood that the curved line at which the cone m intersects the plane S takes the form of an ellipse.

An ellipse is defined when two of the three factors, i.e., the major and minor axes, the distance between foci, and the eccentricity are determined. Now the ratio of the major axis to the minor axis of the ellipse will be considered below.

Figure 10:
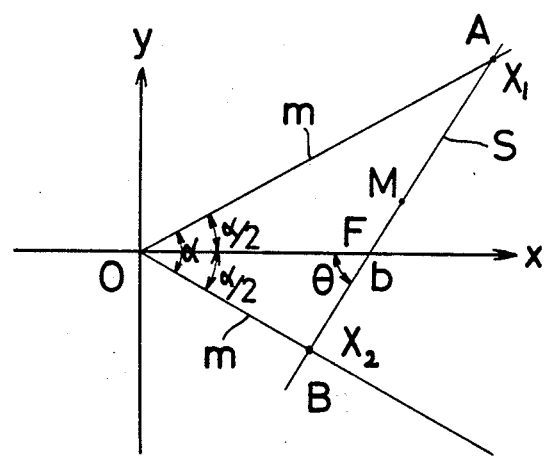
FIG. 10 is a view explaining how a curved line is shaped when the cone formed by lights coming into the end of the image fiber intersects a plane which forms an angle of $\theta$ therewith.

Referring to FIG. 10, the cone m has its vertex disposed on the origin 0 and its axis falling on the axis X. The plane S is assumed to be parallel to the axis Z.

Now the length of the major axis AB of the ellipse is to be found. The plane S forms an angle of $\theta$ with the X axis. The middle point M of the major axis AB is the center of the ellipse. A perpendicular to the XY plane is drawn at the point M. This perpendicular intersects the cone m at points C and D. The line segment CD represents the minor axis.

The line OA can be expressed by $$y = x \tan \alpha/2 \quad (1)$$

The line OB can be expressed by $$y = -x \tan \alpha/2 \quad (2)$$

The line AB can be expressed by $$y = (x-b) \tan \theta \quad (3)$$

where b is the abscissa of the point F at which the line AB intersects the X axis.

From Eq. (1) and (3), the abscissa $x_1$ of the point A is $$x_1 = \frac{b \tan\theta}{\tan\theta - \tan\frac{\alpha}{2}} \quad (4)$$

From Eq. (2) and (3), the abscissa $x_2$ of the point B is $$x_2 = \frac{b \tan\theta}{\tan\theta - \tan\frac{\alpha}{2}} \quad (5)$$

Since the length of the major axis AB is $$AB = (x_1 - x_2) \sec\theta \quad (6)$$

$$AB = \frac{2b \tan\theta \sec\theta \tan\frac{\alpha}{2}}{\tan^2\theta - \tan^2\frac{\alpha}{2}} \quad (7)$$

$$CD = \frac{2b \tan\theta \tan\frac{\alpha}{2}}{\sqrt{\tan^2\theta - \tan^2\frac{\alpha}{2}}} \quad (8)$$

Therefore, the ratio R of the length of major axis to the length of minor axis is $$R = \frac{AB}{CD} = \frac{\sec\theta}{\sqrt{\tan^2\theta - \tan^2\frac{\alpha}{2}}} \quad (9)$$

In accordance with the present invention, a reflex mirror is used which is not in a perfectly circular form, but in the form of an elongated circle.

The elongated circle as termed herein is used in a broader sense including an ellipse having a long axis such as a major axis and a short axis such as a minor axis which are not equal.

Figure 11:
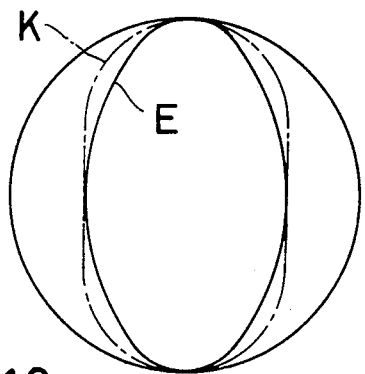
FIG. 11 is a view explaining the terms elongated circle, elliptical, and perfectly circular.

In FIG. 11, E designates an ideal ellipse, while K disignates an elongated circle circumsribing the ellipse E at both ends of the major and minor axes. Such an elongated circle cannot be expressed by a quadratic formula, but can be expressed by an equation made up by adding a term or terms of even-numbered degrees to an equation representing an ellipse.

Because the light is reflected in an even number of times, the image coming into the eye of a viewer is free from bilateral reversal. The object can be inspected in a magnified form. Precise inspection and diagnosis are possible.

Because a reflex mirror in the form of an elongated circle is employed, the present invention has the following advantages:

(1) A wide-angle visual field is afforded by a small reflex mirror.

(2) The mirror with a slender surface can be easily inserted into a confined portion. Especially it is suited for the inspection of an oral cavity.

The device in accordance with the present invention can be used for the following applications:

(1) Inspection of an oral cavity, etc. in dentists' and other physicians' offices (2) Inspection of the interior of a gas pipe, a water pipe, a tube in a heat exchanger, etc.

(3) Inspection of a confined portion in civil engineering and construction work, maintenance of equipment, etc.

What are claimed are:

1. A device for observing pictures of an object comprising an image transmission line for transmitting an image, an optical system for forming the image of the object at the front end of said image transmission line, a reflex mirror for reflexing the light from the object and directing it toward said optical system, said reflex mirror being in the form of an elongated circle having a minor axis perpendicular to the axis of said image transmission line and a major axis perpendicular to said minor axis, the ratio of the length of said major axis to that of said minor axis is equal to $$\frac{\sec\theta}{\sqrt{\tan^2\theta - \tan^2\frac{\alpha}{2}}}$$

wherein $\theta$ is an angle formed between an extension of the axis of said image transmission line and the surface of said reflex mirror, and $\alpha$ is the vertical angle of the conic portion of the light reflected by said reflex mirror, a flexible cable accommodating said image transmission line, and an image receiving means provided at an end of said image transmission line for observing the image transmitted, said image transmission line having an image fiber comprising a bundle of optical element fibers.

2. The device as claimed in claim 1, wherein a light quide for illumination is provided so as to be parallel to said image fiber.

3. The device as claimed in claim 1, wherein the image of the object is reflected in an even number of times.

4. The device as claimed in claim 3, wherein a reflex mirror is provided in said image receiving means.

5. A device as set forth in claim 1 wherein the reflex mirror has the shape of an ellipse.

6. A device as set forth in claim 5 wherein the reflex mirror is supported remotely from the front end of the image transmission line and externally thereof.

* * * * *